US012680071B2

(12) United States Patent
Kraetschmer

(10) Patent No.:  US 12,680,071 B2
(45) Date of Patent:  Jul. 14, 2026

(54) DEVICE AND METHOD FOR CONTROLLING A MICROORGANISM CONTENT

(71) Applicant: c-square bioscience GmbH, Langenlebarn (AT)

(72) Inventor: Gerald Kraetschmer, Sieghartskirchen (AT)

(73) Assignee: c-square bioscience GmbH, Langenlebarn (AT)

( * ) Notice: Subject to any disclaimer, the term of this patent is extended or adjusted under 35 U.S.C. 154(b) by 522 days.

(21) Appl. No.: 18/273,166

(22) PCT Filed: Feb. 8, 2021

(86) PCT No.: PCT/AT2021/060047
§ 371 (c)(1),
(2) Date: Jul. 19, 2023

(87) PCT Pub. No.: WO2022/165541
PCT Pub. Date: Aug. 11, 2022

(65) Prior Publication Data
US 2024/0052294 A1     Feb. 15, 2024

(51) Int. Cl.
*C12N 1/00*          (2006.01)
*C12M 1/12*          (2006.01)
(Continued)

(52) U.S. Cl.
CPC .............. *C12N 1/00* (2013.01); *C12M 37/00* (2013.01); *C12M 41/26* (2013.01); *C12M 41/32* (2013.01); *C12M 41/36* (2013.01); *C12M 41/48* (2013.01)

(58) Field of Classification Search
CPC ...... C12N 1/00; C12N 15/01; C12N 15/0656; C12N 15/1031; C12N 15/1459;
(Continued)

(56) References Cited

U.S. PATENT DOCUMENTS

| | | | | |
|---|---|---|---|---|
| 2002/0042092 A1* | 4/2002 | Banks | ...................... | C12Q 1/04 |
| | | | | 435/39 |
| 2018/0259440 A1* | 9/2018 | Otsuka | ................... | G01N 15/14 |

FOREIGN PATENT DOCUMENTS

| | | |
|---|---|---|
| DE | 66912472 T2 | 8/2004 |
| EP | 0203892 A2 | 12/1986 |

(Continued)

OTHER PUBLICATIONS

International Preliminary Report on Patentability corresponding to International Application No. PCT/AT2021/060047, dated Aug. 3, 2023.

(Continued)

*Primary Examiner* — Michael L Hobbs
(74) *Attorney, Agent, or Firm* — Hoffmann & Baron, LLP

(57)                ABSTRACT

A device for carrying out a method for controlling a content of microorganisms in a liquid includes a measuring unit, a control unit, a supply unit and a computing unit. The measuring unit measures the microorganism content. The control unit determines a dosage of a biocide on the basis of the measured microorganism content using a model with at least one parameter, in order to achieve a predefined microorganism content. The supply unit supplies the biocide to the liquid in the dosage determined by the control unit. The computing unit calculates the at least one parameter from a recording of the microorganism content measured by the measuring unit over at least one past time interval and the amount of biocide supplied in this time interval.

16 Claims, 4 Drawing Sheets

(51) Int. Cl.
  *C12M 1/34*    (2006.01)
  *C12M 1/36*    (2006.01)

(58) Field of Classification Search
  CPC ...... C12M 37/00; C12M 41/26; C12M 41/32;
     C12M 41/36; C12M 41/48; C12Q 1/02;
      C12Q 1/04; G01N 15/0656; G01N
      15/1031; G01N 15/1459; G01N 33/569;
      G01N 2015/1006; G01N 2015/1486;
              G16H 50/20
  See application file for complete search history.

(56) References Cited

FOREIGN PATENT DOCUMENTS

| | | | |
|---|---|---|---|
| EP | 0822261 | A1 | 2/1998 |
| EP | 1133228 | B1 | 7/2002 |
| EP | 1350431 | A1 | 10/2003 |
| EP | 1938690 | A1 | 7/2008 |
| EP | 3617691 | A1 | 3/2020 |
| JP | H11-57731 | A | 3/1999 |
| WO | 97/48822 | A1 | 12/1997 |
| WO | 99/34013 | A1 | 7/1999 |
| WO | 2010/111639 | A1 | 9/2010 |

OTHER PUBLICATIONS

Flemming, H-C., "Biofouling in Water Systems-Cases, Causes and Countermeasures," Applied Microbiology and Biotechnology, vol. 59, pp. 629-640 (2002).
Klahre, Joachim, et al., "Monitoring of Biofouling in Papermill Process Waters," Water Research, vol. 34, No. 14, pp. 3657-3665 (2000).
PCT International Search Report corresponding to International Application No. PCT/AT2021/060047, dated Oct. 25, 2021.
Notice of Submission of Opinion (and English translation) issued in Korean Application No. 10-2023-7027396 on Aug. 25, 2025.
JP Office Action corresponding to Japanese patent application No. 2023-572043, Feb. 17, 2025 with English Translation.

* cited by examiner

DEVICE AND METHOD FOR CONTROLLING A MICROORGANISM CONTENT

CROSS-REFERENCE TO RELATED APPLICATIONS

This application is a National Phase application of International Application No. PCT/AT2021/060047 filed Feb. 8, 2021, the disclosure of which is incorporated herein by reference.

TECHNICAL FIELD

The present disclosed subject matter relates to a device for controlling a content of microorganisms in a liquid, wherein the device comprises a measuring unit for measuring said microorganism content, a control unit connected to the measuring unit and configured to determine a dosage of a biocide on the basis of the measured microorganism content in order to obtain a predefined microorganism content, and a supply unit connected to the control unit and configured to supply the biocide to the liquid in the dosage determined by the control unit. The disclosed subject matter further relates to a method for controlling the microorganism content in the liquid.

BACKGROUND

In a large number of industrial processes and procedures, liquids are used that are undesirably contaminated with microorganisms during their use, for example in the chemical, building materials or food industries during cleaning or cooling or in the production or processing of, for example, beverages, sugar, starch, paper, cellulose, wood materials, coolants or lubricants, paints, building materials or in the fermentation of, for example, amino acids, antibiotics, yeast, citric acid, bioethanol, in beverage bottling, water and waste water treatment, etc. The processes run in batches, for example, wherein the liquid is in an open or closed container, for example a process tank, and is stirred or remains largely stationary. In other processes, the liquid flows continuously through channels or pipes, for example between an inlet and an outlet or in a circuit. In any case, as a result of its composition and/or the industrial process and the containers used therein, undesirable microorganisms, for example algae, bacteria, fungi, especially yeasts, etc., continuously form in the liquid and contaminate it and/or cause stubborn deposits, a so-called "biofilm", or corrosion in the container.

To prevent an excessive microorganism content in the liquid, a biocide is added to the liquid, i.e. an agent with an anti-microbial effect. Generally, the biocide is added continuously; optionally, the biocide is added in individual doses.

Since in the above-mentioned industrial processes, on the one hand, the content of microorganisms in a liquid and, on the other hand, the effect of a biocide supplied to the liquid on the microorganism content change only slowly, it is common practice today in many cases to take samples of the liquid for example once or several times a day, to analyse them for their microorganism content, and then to add a corresponding amount of biocide manually or at least to adjust the supply, for example a pump, manually and to maintain it until the next sample is taken. This procedure is conditional, at least among other things, on the often slow analytical methods employed. For this reason, the biocide is generally dosed at a high level, since the usually exponential growth of the microorganisms may all too quickly lead to an excessive microorganism content if the dosage is too low. However, overdosing has negative effects, for example on the environment as a result of liquid contaminated with biocide and/or on process costs as a result of the high biocide input or necessary subsequent purification of the liquid from biocide, for example in biological wastewater treatment.

In view of new, faster methods for measuring the microorganism content, for example according to the principle of quantitative PCR ("qPCR"), the adenosine triphosphate (ATP) test, next generation sequencing ("NGS"), Raman spectroscopy or flow cytometry, it is now possible to automatically control the supply of biocide depending on the measured microorganism content. For example, a method is known from EP 1 350 431 A1 in which an analysis system determines the microorganisms contained in the liquid and a downstream biocide selection system determines suitable biocides and their concentration on the basis of the determined microorganisms by selecting them from a database and specifies them to a controller, which supplies the biocides in the determined concentration to the liquid in a controlled manner.

Although such an automatic control enables a faster reaction to an increasing microorganism content or to a lack of reduction of the microorganism content as a result of the biocide supply and thus also a more targeted, i.e. also lower, biocide use compared to manual supply, the method or the database used must be adapted to the liquid/s and microorganisms used or occurring in the specific industrial process, i.e. the method is not flexible in its applicability. Furthermore, the biocides and concentrations stored in the database correspond to those used in the case of manual supply, so that the biocides supplied in these processes are, in any case, also usually overdosed in order to prevent an excessive microorganism content.

BRIEF SUMMARY

The disclosed subject matter aims to provide a device and a method for controlling the content of microorganisms in a liquid, which may be used simply, flexibly and reliably for different industrial processes, different liquids and different microorganisms, while avoiding an overdosing of biocide.

According to a first aspect of the disclosed subject matter, this objective is achieved with a device of the type mentioned at the outset, which is distinguished by a computing unit connected to the measuring unit and the control unit, wherein the control unit is configured to determine the dosage using a model with at least one parameter of the relationship between an amount of biocide supplied in a time interval and the change in the microorganism content caused thereby in this time interval, and wherein the computing unit is configured to calculate, from a recording of the microorganism content measured by the measurement unit over at least one past time interval and the amount of biocide supplied in that time interval, the at least one parameter for use by the control unit in at least one subsequent time interval.

The model is a kinetic model of the reaction of the liquid, i.e. the change in its microorganism content, to the amount of biocide added; thus, reactions of all liquids contaminated with microorganisms to the addition of biocide may be modelled. With the help of the computing unit, the model is adapted, i.e. tracked, to different liquids and, above all, to the dynamic changes of a liquid with the microorganisms contained therein or their reaction to the biocide supply by simple calculation of the parameter/s. By using this param-
eterised model of the reaction, the device or its control unit
simultaneously adapts to the respective process and the
liquid used or occurring therein and the microorganisms
contained therein, and the control is tracked. The device of
the disclosed subject matter is thus particularly simple and
flexible in use and controls the microorganism content of the
liquid particularly effectively, thus saving considerable
amounts of biocide.

In an advantageous embodiment, said model is given by
the equation $$\frac{dX}{dt} = -kB^n X$$

with:

$$\frac{dX}{dt}$$

change in microorganism content in a time interval,
k parameter of the model,
B amount of biocide supplied in this time interval,
n dilution coefficient of the biocide and
X measured microorganism content.

This represents a particularly simple and universally
applicable model the parameters of which may be deter-
mined with little effort. The dilution coefficient of the
biocide may either be known in advance, for example if the
biocide used and the liquid or the microorganisms contained
therein are known with sufficient accuracy, or it is calculated
by the computing unit as a further parameter of the model;
the computing unit calculates such further parameters for
example from the recording over at least a correspondingly
large number of further past time intervals.

The same applies to an alternative embodiment, according
to which the stated model is given by the equation $$\frac{dX}{dt} = -k_1 B_0^n e^{-k_2 nt} X$$

with:

$$\frac{dX}{dt}$$

change in microorganism content in a time interval,
$k_1$, $k_2$ parameters of the model,
$B_0$ amount of biocide supplied in this time interval at the
time of its supply,
n dilution coefficient of the biocide and
X measured microorganism content.

This extended kinetic model takes into account the pos-
sible property of a biocide to be broken down or inactivated
over time after its supply to the liquid.

The measuring unit may measure the content of micro-
organisms in the liquid in various ways, for example accord-
ing to the principle of quantitative PCR ("qPCR"), the
adenosine triphosphate (ATP) test, next generation sequenc-
ing ("NGS") or Raman spectroscopy. It is particularly
advantageous if the measuring unit is a flow cytometer
which is configured to measure the content of microorganisms of a predetermined type. Flow cytometers allow a
parallel evaluation of several measuring channels at high
speed, i.e. also in real time, and at the same time a differ-
entiation of the microorganisms on the basis of different
fluorescence, structure, colour, electrical properties, etc.
with the optional aid of different fluorescent dyes. In the
flow cytometer, the microorganisms are individually guided
in rapid succession along a high electrical voltage and/or
through a laser beam and their respective specific reaction to
the electrical field (for example deflection) and/or the laser
beam (for example reflection, colour, fluorescence, etc.) is
detected and evaluated. In most cases, multi-dimensional
data fields are generated, in which the detected microorgan-
isms are automatically classified, for example by (multi-
dimensional) cluster formation, and are thus differentiated.
In this way, the microorganisms of the predetermined type
may be found and selectively counted. For classification, a
learning system may optionally be used, as known from EP
3 617 691 A1.

It is particularly favourable when the computing unit is
configured to calculate the at least one parameter after each
time interval of a sequence of time intervals from the
recording of the microorganism content measured by the
measuring unit over at least one immediately preceding time
interval and the amount of biocide supplied in this at least
one immediately preceding time interval. The at least one
parameter of the model is thereby continuously tracked, so
that the control is immediately adapted to any change in the
property of the liquid contaminated with the microorganisms
and thereby achieves a particularly good effect. The time
intervals of the sequence may be adapted here to the
respective requirements and are dependent in particular on
how quickly the liquid changes its properties.

In an optional embodiment of the device, the supply unit
is configured to select the biocide from one or more com-
ponents according to a predetermined composition, wherein
the device further comprises a control unit which is con-
nected to the supply unit and which is configured to prede-
termine the composition for the supply unit. This enables
optimisation beyond the dosage in order to use a biocide
formed of one or more components that is particularly
effective for the measured content and the measured type/s
of microorganisms.

It is particularly favourable if the device comprises at
least one sensor for measuring at least one of the measurands
constituted by pH, temperature, pressure and conductivity of
the liquid, wherein the control unit is connected to the at
least one sensor and is configured to predetermine the
composition depending on at least this/these measurand/s.
The biocide is thereby optimised on the basis of concretely
measured liquid properties, which, for example, have an
influence on the content of microorganisms in the liquid,
according to experience. For example, the biocide may on
the one hand contain, in addition to at least one antimicrobial
component, at least one component with a different effect,
which influences, for example, the pH value or the conduc-
tivity of the liquid, so that the antimicrobial component of
the biocide is particularly effective; on the other hand,
different antimicrobial components may be combined. The
composition may be predetermined and selected according
to the measured parameter/s or according to other aspects,
for example the microorganism content in the liquid, the
environmental friendliness of the components and/or their
cost. The stated selection includes, in the case of two or more
components, mixing them or dissolving one component in
the other; or the selected components are supplied separately
to the liquid.

It is particularly advantageous if the control unit is configured to predetermine a composition for the supply unit at regular time intervals. If no change in the composition is required, the control unit may also predetermine the same composition several times in succession. Furthermore, at least occasionally, a random composition of the biocide may be predetermined, whereby the control unit may test the effectiveness of different compositions and—for example if the control unit is a self-learning system—may learn so that it may later predetermine an optimal composition on the basis of what it has learned.

In a second aspect, the disclosed subject matter provides a method for controlling the level of microorganisms in a liquid, comprising in a control process:

measuring said microorganism content with the aid of a measuring unit, determining a dosage of a biocide with a view to achieving a predefined microorganism content on the basis of the measured microorganism content and a model comprising at least one parameter of the relationship between an amount of biocide supplied in a time interval and the change in microorganism content caused thereby in that time interval, and supplying the biocide in the determined dosage to the liquid; and in a tracking process parallel or intermittent to the control process:

calculating the at least one parameter from a recording of the microorganism content measured by the measuring unit over at least one past time interval and the amount of biocide supplied in that time interval for use in the control process in at least one later time interval.

Regarding the advantages of the method and further variants, reference is made to the previous explanations relating to the device.

BRIEF DESCRIPTION OF THE DRAWINGS

The disclosed subject matter is explained in greater detail below with reference to exemplary embodiments shown in the accompanying drawings. In the drawings.

DETAILED DESCRIPTION

Figure 1:
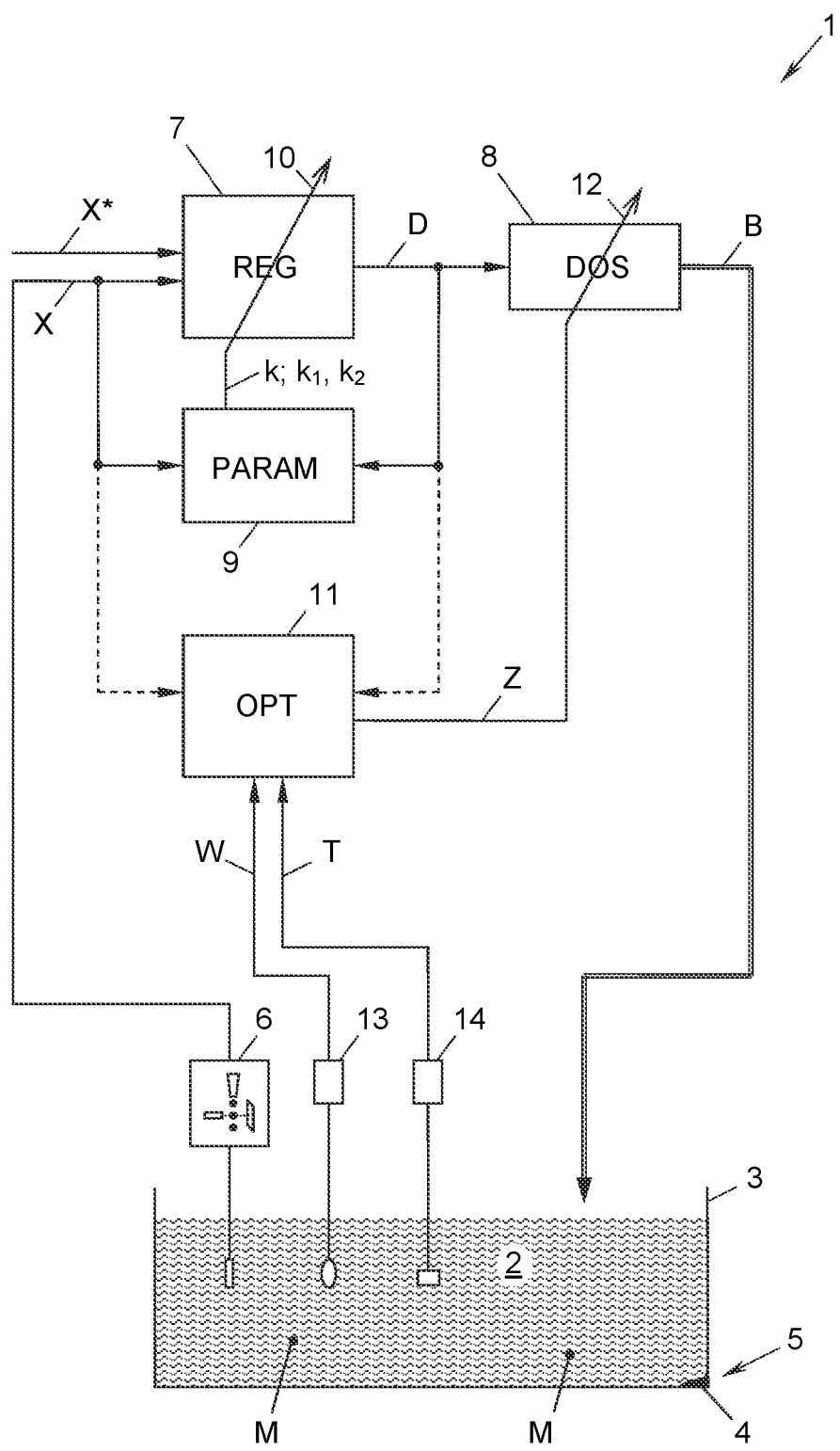
FIG. 1 shows a device according to the disclosed subject matter for controlling a content of microorganisms in a liquid in a block diagram.

A device 1 according to FIG. 1 controls a content X of microorganisms M in a liquid 2 in order to achieve a predefined microorganism content X*. The microorganisms M are, for example, algae, bacteria, fungi, in particular yeasts, etc. The liquid 2 is used, for example, in an industrial process for the production, processing, cooling, cleaning or the like of an object or a substance or is the actual process object—for example in the form of a beverage in a filling plant. The industrial process may be a batch process here, in which the liquid 2 is produced or used in batches, or it may be a continuous process in which the liquid 2 is also used continuously.

The liquid 2 is in a container (here: an open tank) 3, and microorganisms M have—in this example—formed an unwanted deposit 4 in a corner 5 of the tank 3 as a result of their multiplication. Alternatively, microorganisms M multiply in the liquid without forming a deposit 4 and contaminate the liquid 2 or are undesirable for other reasons.

A measuring unit 6 measures said microorganism content X in the liquid 2. The content X indicates the number of microorganisms M per reference quantity of the liquid 2, i.e. per volume (for example millilitre), per mass (for example gram) or per quantity (for example mole) of the liquid 2. To measure the microorganism content X, the measuring unit 6 may use different methods, for example a quantitative PCR ("qPCR"), an adenosine triphosphate (ATP) test, a next generation sequencing ("NGS") measurement method or a Raman spectroscopy. In the case shown, the measuring unit 6 is a flow cytometer which measures the content X of microorganisms M of a predetermined type A, as explained in greater detail below using the example of FIG. 2.

In a flow cytometer, particles are passed individually in rapid succession past a high electric voltage and/or a laser beam and their respective specific reaction to the electric field (for example deflection) and/or the laser beam (for example reflection, colour, fluorescence, etc.) is detected and evaluated. Flow cytometers allow a parallel evaluation of several measuring channels at high speed, i.e. also in real time, and distinguish particles according to their properties or reactions; optionally, auxiliary substances, for example fluorescent dyes, are used here. In most cases, multi-dimensional data fields are generated, in which the detected particles may be automatically classified, for example by (multi-dimensional) cluster formation, and then optionally counted, for example by class. In this way, the type A of microorganisms M of which the content X is to be (selectively) measured in the liquid 2 may optionally be predetermined.

Figure 2:
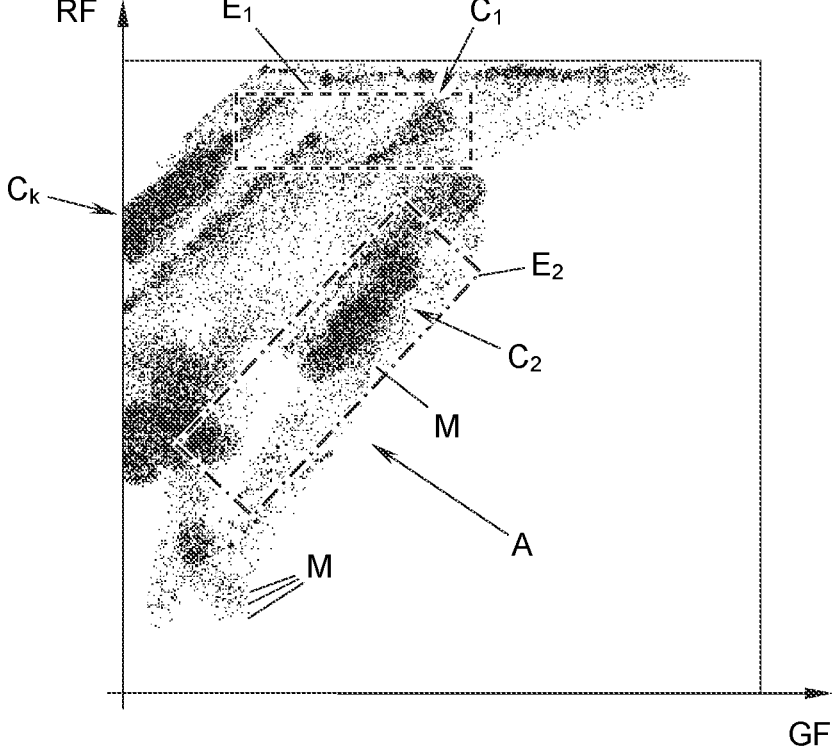
FIG. 2 shows a diagram of the fluorescence properties of microorganisms detected with a measuring unit of the device from FIG. 1.

The exemplary two-dimensional diagram in FIG. 2 shows microorganisms M that were detected by flow cytometry, differentiated according to their properties (in this case two properties, namely red and green fluorescence) and recorded. In the diagram, the green fluorescence is plotted horizontally and the red fluorescence vertically (here: in each case on a logarithmic scale). Further physical or chemical properties (for example other fluorescences, etc.) may be detected on further measuring channels and for example evaluated in further dimensions. Microorganisms M with similar properties (here: in these two wavelength ranges) each form clusters $C_1$, $C_2$, . . . , generally $C_k$, in the diagram. By means of known clusters $C_k$ or those determined with the aid of a learning cluster evaluation, different microorganisms M may be distinguished from each other; for example, in the diagram of FIG. 2 algae are marked by a dashed rectangle $E_1$ and distinguished from bacteria (dot-and-dash rectangle $E_2$). Therefore, either algae or (in this case) bacteria, etc. may be predetermined as the abovementioned type A. Alternatively, certain algae, for example blue-green algae, or certain bacteria, for example lactic acid bacteria, etc., or a type A of microorganisms M with special properties may be predetermined as the abovementioned type A, insofar as these may be distinguished in the flow cytometry, for example it could be differentiated by the predetermined type A whether a microorganism M is viable or not, and only the viable microorganisms M could be predetermined as type A. Lastly, different microorganisms M, for example algae and bacteria, may be predetermined together as type A.

When, in the case of FIG. 2, for example, the stated bacteria are predetermined as the type A, the measuring unit 6 measures their content X in the liquid 2, i.e. other microorganisms M or particles that are not microorganisms M at all are not taken into account further by the measuring unit 6 when measuring the microorganism content X in this example. From diagrams of successive time intervals Δt, a change in the microorganisms M, in particular their content X, in the liquid 2 over time may be determined.

It is understood that the measuring unit 6 measures the microorganism content X generally from a sample of liquid 2 taken from the container 3.

Returning to the device 1 of FIG. 1, a control unit 7 is connected to the measuring unit 6 so that it has access to the microorganism content X measured by the measuring unit 6 in each case. The control unit 6 has, for example, a proportional integral (PI), a proportional integral differential (PID) controller or the like for controlling the microorganism content X. For this purpose, the control unit 7 determines a dosage D of a biocide B which is to be added to the liquid 2 in order to achieve the predefined microorganism content X*. The predefined microorganism content X* may be predefined here to be constant on the one hand or to vary over time on the other hand. The temporal variation of the predefined microorganism content X* is based, for example, on an adaptation to a previously planned course and/or a measured state of the industrial process. For example, in the context of a so-called "fed-batch" process successively supplying liquid 2—for example in a fermentation process—not only the amount of liquid 2 depends on the process progression, i.e. varies over time, but usually also the predefined microorganism content X*; in particular, the quantity of liquid may be small and a, for example, high predefined microorganism content X* may be desired in an initial stage of the process, whereas in a later stage of the process the quantity of liquid is larger and the predefined microorganism content X* is to be reduced.

The device 1 further comprises a supply unit 8 with one or more reservoirs from which it supplies biocide B to the liquid 2, for example by means of a controllable pump or a control valve. The supply unit 8 is connected to the control unit 7 to supply the biocide B to the liquid 2 in the dosage D determined by the control unit 7.

In order to determine the dosage D, the control unit 7 uses a model with at least one parameter k. The model represents a relationship between an amount P of biocide B supplied in a time interval Δt and the change in the microorganism content X caused thereby in this time interval Δt, i.e. it is a kinetic model of the reaction of the liquid 2 and thus of its microorganism content X to the biocide B supplied. It is understood that the amount P of biocide B supplied in the time interval Δt coincides with the dosage D of biocide B to be supplied to the liquid 2 if this has been determined for the same time interval Δt. The control unit 7 uses the model to adapt one or more time constants and/or gains of its controller to the reaction of the liquid 2, i.e. the change in its microorganism content X, to biocide supply.

The model may be of various types, in particular a model that assumes a linear, quadratic or exponential decrease in the microorganism content X with biocide addition. In one embodiment, the model is given by the following equation 1:

$$\frac{dX}{dt} = -kB^n X \tag{1}$$

with:

$$\frac{dX}{dt}$$

change in microorganism content X in a time interval Δt (here: the "infinitesimal" time interval dt),
k parameter of the model concerning a deactivation of the microorganisms M,
B amount P of biocide B supplied in this time interval Δt,
n dilution coefficient of the biocide B and
X measured microorganism content X.

In an alternative embodiment, the model is given by the following equation 2:

$$\frac{dX}{dt} = -k_1 B_0^n e^{-k_2 nt} X \tag{2}$$

with:

$$\frac{dX}{dt}$$

change in microorganism content X in a time interval Δt (here: the "infinitesimal" time interval dt),
$k_1$ parameter of the model concerning a deactivation of the microorganisms M,
$k_2$ parameter of the model concerning an inactivation of biocide B after its supply to the liquid 2,
$B_0$ amount P of biocide B supplied in this time interval Δt at the time of its supply,
n dilution coefficient of the biocide B and
X measured microorganism content X.

The extended model of equation (2) makes it possible, through the parameter $k_2$, to take into account an inactivation of the biocide B after its supply to the liquid 2.

In both of the above-mentioned models, the dilution coefficient n of the biocide B is either known in advance if the biocide B used and the liquid 2 and the microorganisms M contained therein are known; otherwise, the dilution coefficient n is another parameter of the model, so that the model given by equation (1) has two parameters k and n and the model given by equation (2) has three parameters $k_1$, $k_2$ and n.

If the model is also to represent an influence of any side reactions of the industrial process on the relationship between the amount P of biocide B supplied and the change in the microorganism content X caused thereby, the model may optionally be given, for example, by a system of coupled differential equations, which in each case describe the influence of the industrial process itself or that of its side reactions.

In order to adapt the model or its at least one parameter k, $k_1$, $k_2$, n and thus the control unit 7 to the reaction of the liquid 2 to biocide supply and also to track it in the event of dynamic changes in this reaction, the device 1 has a computing unit 9 which is connected to the measuring unit 6 and the control unit 7 and which tracks the control unit 7 via a control path 10. The computing unit 9 calculates the parameter/s k or $k_1$, $k_2$ etc. (and, if necessary, the dilution coefficient n as a further parameter) of the respective model and, for this purpose, uses a recording of the microorganism content X measured by the measuring unit 6 over at least one past time interval $\Delta t$ and an amount P of biocide B which was supplied to the liquid 2 in this time interval $\Delta t$, as will be explained in greater detail below with reference to the example of FIG. 3, which relates to a model with a parameter k. It is understood that in the case of a model with two or more parameters $k_1$, $k_2$, n, . . . the computing unit 9 may calculate them from recordings of at least a corresponding number of previous time intervals $\Delta t$.

Figure 3:
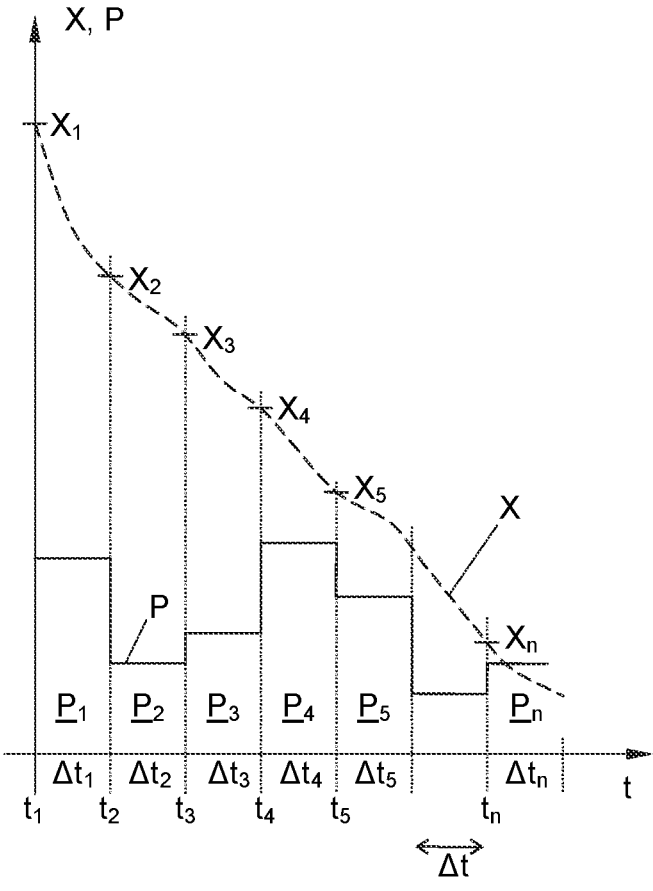
FIG. 3 shows a graph of the biocide supply and the microorganism content in the liquid over time using the device from FIG. 1.

FIG. 3 shows a sequence of time intervals $\Delta t_1$, $\Delta t_2$, . . . , generally $\Delta t_n$, which each lie between two times $t_1$, $t_2$, . . . , generally $t_n$. At least at each time $t_n$, the measuring unit 6 measures the microorganism content $X_1$, $X_2$, . . . , generally $X_n$ (here: a continuously measured progression of the microorganism content X). In each time interval $\Delta t_n$ of the sequence, an amount $P_1$, $P_2$, . . . , generally $P_n$, of biocide B is supplied in each case (here: continuously during each time interval $\Delta t_n$). If, for example, an amount $P_4$ of biocide B is added to the liquid 2 in a time interval $\Delta t_4$ between the times $t_4$ and $t_5$, this causes a change in the microorganism content X from a value $X_4$ at the time $t_4$ to a value $X_5$ at the time $t_5$.

Said parameter k of the model may be calculated by the computing unit 9 after any or after each time interval $\Delta t_n$ of the sequence. If, for example, the parameter k is to be calculated for the time interval $\Delta t_4$, the computing unit 9, after this time interval $\Delta t_4$ has elapsed, takes the microorganism content $X_4$ measured by the measuring unit 6 over this time interval $\Delta t_4$ from the recording (FIG. 3) and the amount $P_4$ of biocide B supplied during this time interval $\Delta t_4$. The parameter k is calculated on the basis of this amount $P_4$ and the change $\Delta X$ (or infinitesimal: dX) of the microorganism content X (for example according to $\Delta X = X_5 - X_4$) caused thereby and is transmitted to the control unit 7 for use by it in one or more later time intervals $\Delta t_n$ (here: for example $\Delta t_5$ and/or $\Delta t_6$).

Optionally, the computing unit 9 may contain an adjustment device which averages or adjusts the calculated parameter k with values of the parameter k calculated for previous time intervals $\Delta t$ by—for example weighted—averaging before transfer to the control unit 7. The adjustment device is, for example, an additional computing module of the computing unit 9 or a neural network, in particular a Long Short-Term Memory (LSTM), which during the adjustment optionally additionally takes into account changes in the microorganism content X caused in previous time intervals $\Delta t$. In this case, the control unit 7 uses the adjusted parameter k of the model to adjust its controller, whereby past parameter changes are taken into account and a sudden adjustment of the controller is prevented.

Referring back to FIG. 1, in an optional embodiment the delivery unit 8 is configured to select the biocide B from one or more components, each of which the delivery unit 8 holds in a reservoir, in order to achieve a predetermined composition Z of the biocide B. In this embodiment, the device comprises a control unit 11, which is connected to the supply unit 8 and predetermines said composition Z for the supply unit 8. The control unit 11 thus intervenes in the supply of the biocide B, for example by predetermining or changing the composition Z of the biocide B via a control path 12.

The composition Z may optionally be predetermined here randomly—at least occasionally; alternatively, the components of the composition Z are selected heuristically, for example, as will be explained in greater detail below. Optionally, the device 1 comprises for this purpose one or more (in the example of FIG. 1: two) sensors 13, 14, which measure at least one measurand (usually one measurand per sensor 13, 14), for example the pH W, the temperature T, the pressure and/or the conductivity of the liquid 2. In the example of FIG. 1, one sensor 13 of said sensors 13, 14 measures the pH W and the other sensor 14 measures the temperature T of the liquid 2. In this case, the control unit 11 predetermines the composition Z depending on at least said measurands W, T.

When predetermining the composition Z of the biocide B, the control unit 11 is further optionally connected to the measuring unit 6 to predetermine the composition Z also depending on the microorganism content X. Furthermore, the control unit 11 is optionally connected to the control unit 7 to obtain the dosage D determined by the latter, so that the control unit 11 may predetermine the composition Z also depending on the dosage D or the amount P of biocide B supplied in the time interval $\Delta t$, depending on the parameter/s k, $k_1$, $k_2$, n calculated therefrom, and/or depending on the change in the microorganism content X as a result of the biocide supply. Moreover, the control unit 11 may take into account other information, for example an environmental compatibility and/or the cost of each of the components, and may predetermine the composition Z in dependence thereon.

All of these dependencies are stored, for example, in a database as heuristics, which belong to the control unit 11 so that it may predetermine a suitable composition Z based on heuristics. Alternatively, the control unit 11 optionally has a self-learning system, for example a neural network, in particular a Long Short-Term Memory (LSTM), which learns from compositions Z predetermined in the past the resulting amounts P of biocide B added or the changes in the microorganism content X caused thereby. On the basis of the respective measured values of the sensors 13, 14 or the measuring unit 6 and/or any further of said information and the heuristics, the control unit 11 then predetermines a particularly suitable—for example particularly effective, environmentally friendly, cost-effective—composition Z of the biocide B in each case. For this purpose, the system may at least occasionally predetermine random compositions Z.

Figure 4:
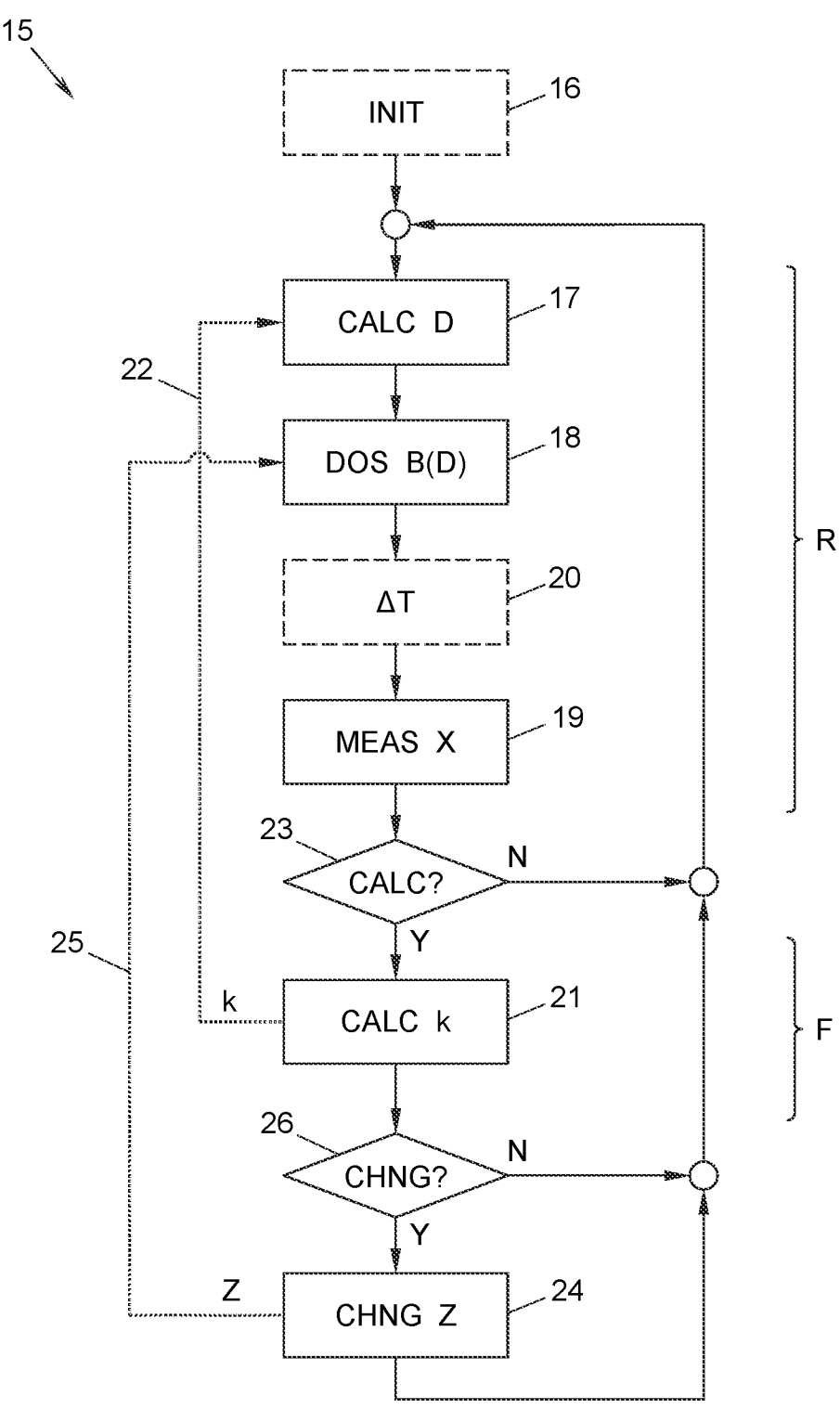
FIG. 4 shows an exemplary method executed by the device from FIG. 1 for controlling the microorganism content in the liquid in a flow chart.

With reference to the example shown in FIG. 4, various examples of a method 15 carried out by the device 1 for controlling the microorganism content X in the liquid 2 are explained in greater detail below.

In an initialisation step 16, the parameter/s k or $k_1$, $k_2$ of the model including the dilution coefficient n and the microorganism content X* to be achieved are predefined and the microorganism content X of the liquid 2 is measured. A control process R of the method 15 is then either continuously executed, for example with the aid of analogue controller components, or is run through cyclically, in particular periodically—as in the example shown—as a digital control process R. As described above, the control process R comprises at least one step 17, in which the control unit 7 determines the dosage D of the biocide B, a step 18, in which the supply unit 8 supplies the biocide B to the liquid 2 in the dosage D determined in step 17 and optionally selects the composition Z, and a step 19, in which the measuring unit 6 measures the microorganism content X in the liquid 2.

If the control process R is run through cyclically—as shown—the supply unit 8 may in step 18 either immediately supply the entire dose of the dosage D of biocide B determined by the control unit 7 to the liquid 2 or may cause the biocide B to be added to the liquid 2 continuously, for example with the aid of a pump, in the determined dosage D.

In order to take into account a merely slow change in the microorganism content X after the biocide B has been supplied 18, the control process R optionally contains a waiting step 20 so that a changed microorganism content X may already be expected during the following measurement 19.

In a tracking process F, the computing unit 9 calculates the parameter/s k, $k_1$, $k_2$, n of the model in step 21 as previously described. The calculated parameter/s k, $k_1$, $k_2$, n of the model is/are used to track the control unit 7 or its controller via path 22 (to step 17). The tracking process F may be carried out in parallel with the control process R or—as shown—intermittently, i.e. interrupting the control process R in each case. In the variant shown, the tracking process F immediately follows the control process R, i.e. it interrupts the control process R if a positive check is carried out in a branch 23 (branch "Y" of branch 23); if a negative check is carried out (branch "N" of branch 23), the control process R continues to be executed. The test criterion used in branch 23 is, for example, a number of runs of the control process R since the last run of the tracking process F, the expiry of a period of time, for example the time interval Δt, or a particularly high value for, for example, the dosage D determined by the control unit 7 or the microorganism content X measured by the measuring unit 6. Alternatively, the tracking process F may immediately follow the control process R in each cycle, i.e. the process 15 may have no branching 23.

In this context, it should be noted that the time interval Δt may be chosen as required, for example equal to the period of the control process R if this is run periodically, or longer, in particular a multiple thereof.

In an optional step 24, which is carried out in parallel with the control process R and the tracking process F or intermittently thereto—as shown—the control unit 11 determines the composition Z of the biocide B as described above and stipulates this to the supply unit 8 via path 25. In the variant shown, the predetermining 24 immediately follows the tracking process F if a positive check is carried out in a branch 26 (branch "Y" of branch 26); if the check is negative (branch "N" of branch 26), the control process R continues. In general, the composition Z is predetermined at regular time intervals, i.e. reaching the time interval from the last point of being predetermined 24 is used as a test criterion in branch 26. These time intervals are usually considerably larger—for example 10 times or 100 times larger—than the time intervals Δt considered in the control process R and the tracking process F. As an alternative or supplementary test criterion, for example a decrease in the microorganism content X below the threshold value—and thus lower than expected—despite a high dosage D or an exceeding of the threshold value of the microorganism content X or an increase of the latter may be used.

The disclosed subject matter is not limited to the embodiments set out, but encompasses all variants, modifications and combinations thereof which fall within the scope of the accompanying claims.

What is claimed is:

1. A device for controlling a content of microorganisms in a liquid, the device comprising:
a measuring unit for measuring said microorganism content,
a control unit, which is connected to the measuring unit and which is configured to determine a dosage of a biocide based on the measured microorganism content in order to achieve a predefined microorganism content,

12 a supply unit, which is connected to the control unit and which is configured to supply the biocide to the liquid in the dosage determined by the control unit, and
a computing unit connected to the measuring unit and the control unit,
wherein the control unit is configured to determine the dosage using a model with at least one parameter of a relationship between an amount of biocide supplied in a time interval and a change in the microorganism content caused by the supplied amount of biocide in this time interval, and
wherein the computing unit is configured to calculate the at least one parameter for use by the control unit in at least one later time interval from a recording of the microorganism content measured by the measuring unit over at least one past time interval and the amount of biocide supplied in this time interval.

2. The device according to claim 1, wherein said model is given by an equation $$\frac{dX}{dt} = -kB^n X$$

with:

$$\frac{dX}{dt}$$

change in microorganism content in a time interval,
k parameter of the model,
B amount of biocide supplied in this time interval,
n dilution coefficient of the biocide and
X measured microorganism content.

3. The device according to claim 1, wherein said model is given by an equation $$\frac{dX}{dt} = -k_1 B_0^n e^{-k_2 nt} X$$

with:

$$\frac{dX}{dt}$$

change in microorganism content in a time interval,
$k_1$, $k_2$ parameters of the model,
$B_0$ amount of biocide supplied in this time interval at the time of supply,
n dilution coefficient of the biocide and
X measured microorganism content.

4. The device according to claim 1, wherein the measuring unit is a flow cytometer which is configured to measure the content of microorganisms of a predetermined type.

5. The device according to claim 1, wherein the computing unit is configured to calculate the at least one parameter after each time interval of a sequence of time intervals from the recording of the microorganism content measured by the measuring unit over at least one immediately preceding time interval and the amount of biocide supplied in this at least one immediately preceding time interval.

6. The device according to claim 1, wherein the supply unit is configured to select the biocide from one or more components according to a predetermined composition, wherein the device further comprises a control unit which is connected to the supply unit and which is configured to predetermine the composition for the supply unit.

7. The device according to claim 6, wherein the device comprises at least one sensor for measuring at least one measurand comprising pH, temperature, pressure and conductivity of the liquid, wherein the control unit is connected to the at least one sensor and is configured to predetermine the composition depending on at least this/these measurand/s.

8. The device according to claim 6, wherein the control unit is configured to predetermine a composition for the supply unit at regular time intervals.

9. A method for controlling a content of microorganisms in a liquid, the method comprising in a control process:

measuring said microorganism content by means of a measuring unit, determining a dosage of a biocide with a view to achieving a predefined microorganism content based on the measured microorganism content and a model comprising at least one parameter of a relationship between an amount of biocide supplied in a time interval and a change in microorganism content caused by the supplied amount of biocide in that time interval, and supplying the biocide in the determined dosage to the liquid; and in a tracking process parallel or intermittent to the control process:

calculating the at least one parameter from a recording of the microorganism content measured by the measuring unit over at least one past time interval and the amount of biocide supplied in that time interval for use in the control process in at least one later time interval.

10. The method according to claim 9, wherein said model is given by an equation $$\frac{dX}{dt} = -kB^n X$$

with:

$$\frac{dX}{dt}$$

change in microorganism content in a time interval, k parameter of the model,

B amount of biocide supplied in this time interval, n dilution coefficient of the biocide and X measured microorganism content.

11. The method according to claim 9, wherein said model is given by an equation $$\frac{dX}{dt} = -k_1 B_0^n e^{-k_2 nt} X$$

with:

$$\frac{dX}{dt}$$

change in microorganism content in a time interval, $k_1$, $k_2$ parameters of the model, $B_0$ amount of biocide supplied in this time interval at the time of supply, n dilution coefficient of the biocide and X measured microorganism content.

12. The method according to claim 9, wherein the measuring unit measures the content of microorganisms of a predetermined type.

13. The method according to claim 9, wherein the tracking process is carried out after each time interval of a sequence of time intervals, wherein the at least one parameter is calculated from the recording of the microorganism content measured by the measuring unit over at least one immediately preceding time interval and the amount of biocide supplied in this at least one immediately preceding time interval.

14. The method according to claim 9, wherein the biocide is selected from one or more components according to a predetermined composition.

15. The method according to claim 14, wherein at least one sensor measures at least one measurand comprising pH, temperature, pressure and conductivity of the liquid and the composition is predetermined depending on at least this/these measurand/s.

16. The method according to claim 14, wherein a composition is predetermined at regular time intervals.

* * * * *